United States Patent
DeFreitas et al.

(10) Patent No.: US 9,649,068 B2
(45) Date of Patent: May 16, 2017

(54) TABLE FOR PERFORMING MEDICAL PROCEDURES

(75) Inventors: Kenneth F. DeFreitas, Patterson, NY (US); Ian Shaw, Yorktown Heights, NY (US); Kathy Pickett, Uncasville, CT (US); Aaron Fand, Bethel, CT (US); Agnes Mercurio, Longpond, PA (US); Linda Volpe, Narragansett, RI (US); Kelly Farmer, Powhatan, VA (US); Darrin Manke, North Andover, MA (US); Erin-Anne A. Lemieux, Milford, NH (US); Christopher Paul Loughnane, Nashua, NH (US); Christopher Labak, Brookline, NH (US)

(73) Assignee: HOLOGIC, INC., Marlborough, MA (US)

( * ) Notice: Subject to any disclaimer, the term of this patent is extended or adjusted under 35 U.S.C. 154(b) by 940 days.

(21) Appl. No.: 13/985,313

(22) PCT Filed: Nov. 17, 2011

(86) PCT No.: PCT/US2011/061186
§ 371 (c)(1),
(2), (4) Date: Aug. 14, 2013

(87) PCT Pub. No.: WO2012/068373
PCT Pub. Date: May 24, 2012

(65) Prior Publication Data
US 2014/0058286 A1  Feb. 27, 2014

Related U.S. Application Data

(60) Provisional application No. 61/415,022, filed on Nov. 18, 2010.

(51) Int. Cl.
A61B 6/04 (2006.01)
A61G 13/12 (2006.01)
(Continued)

(52) U.S. Cl.
CPC ............ *A61B 5/708* (2013.01); *A61B 6/0407* (2013.01); *A61B 6/0435* (2013.01);
(Continued)

(58) Field of Classification Search
CPC ........ A61G 7/015; A61G 7/018; A61G 7/012; A61G 13/06; A61G 13/08; A61G 13/122;
(Continued)

(56) References Cited

U.S. PATENT DOCUMENTS 1,626,091 A * 4/1927 Macklin ............... A61G 13/009
5/507.1
2,258,782 A * 10/1941 McKean ............ A61G 13/0018
108/77

(Continued)

OTHER PUBLICATIONS

International Search Report and Written Opinion from related PCT application PCT/11/61186 dated Mar. 2, 2012.
(Continued)

*Primary Examiner* — Robert G Santos
(74) *Attorney, Agent, or Firm* — Kriegsman & Kriegsman (57) ABSTRACT

The table for performing breast biopsies is characterized by features that enhance patient comfort and facilitate performance of the biopsy. An opening in the table allowing the breast to extend below the table top is formed in a removable insert. An area of the insert includes padding. An alternate insert having a different diameter opening may be selected based on patient breast size. Another insert having an asymmetrical opening may accommodate the patient's arm when it is desirable to position both the arm and breast of the patient below the table top. The table top is contoured such (Continued)

that symmetrical distal end sections are elevated relative to a central section to support the patient in multiple positions. A removable pad may be placed over the insert. An end portion for padding the hip of the patient is thicker than an end portion for padding the head/neck of the patient.

22 Claims, 8 Drawing Sheets

(51) Int. Cl.
    *A61B 5/00*     (2006.01)
    *A61B 10/02*     (2006.01)
    *A61G 13/00*     (2006.01)
    *A61G 13/08*     (2006.01)

(52) U.S. Cl.
    CPC ...... *A61B 10/0233* (2013.01); *A61G 13/0018* (2013.01); *A61G 13/08* (2013.01); *A61G 13/121* (2013.01); *A61G 13/122* (2013.01); *A61G 13/123* (2013.01); *A61G 13/129* (2013.01); *A61G 13/1285* (2013.01); *A61G 13/1295* (2013.01); *A61G 13/1235* (2013.01); *A61G 2200/12* (2013.01); *A61G 2200/325* (2013.01)

(58) Field of Classification Search
    CPC   A61G 13/1285; A61B 6/0407; A61B 6/0435; A61B 6/04; A61B 5/0091; A61B 5/0555; A61B 6/502; A61B 5/708
    USPC ... 5/621–624, 620, 613, 601, 600, 632, 731, 5/735; 378/208, 209, 37, 20
    See application file for complete search history.

(56) References Cited

U.S. PATENT DOCUMENTS

| | | | | |
|---|---|---|---|---|
| 2,872,259 | A * | 2/1959 | Thorpe | A61G 13/00 5/613 |
| 4,076,230 | A * | 2/1978 | Pike | A61G 13/12 5/600 |
| 4,596,384 | A * | 6/1986 | Blosser | A47G 9/10 5/600 |
| 5,289,520 | A * | 2/1994 | Pellegrino | A61B 6/0435 378/208 |
| 5,400,449 | A * | 3/1995 | Satto | A47C 20/021 5/631 |
| 5,426,685 | A * | 6/1995 | Pellegrino | A61B 6/0435 378/196 |
| 5,609,152 | A * | 3/1997 | Pellegrino | A61B 6/0435 378/37 |
| 6,480,565 | B1 * | 11/2002 | Ning | A61B 6/032 378/20 |
| 6,739,006 | B2 * | 5/2004 | Borders | A61B 6/0457 5/622 |
| 6,754,923 | B2 * | 6/2004 | Borders | A61G 13/101 5/618 |
| 6,883,194 | B2 * | 4/2005 | Corbeil | A61B 5/0091 378/37 |
| 6,886,198 | B2 * | 5/2005 | Marin | A61B 5/0091 378/209 |
| 6,987,831 | B2 * | 1/2006 | Ning | A61B 6/032 378/20 |
| 7,194,778 | B2 * | 3/2007 | Riach | A47C 20/026 5/727 |
| 7,603,730 | B2 * | 10/2009 | Zelnik | A47C 20/00 378/208 |
| 7,636,967 | B1 * | 12/2009 | Stokes | A61G 13/009 5/620 |
| 7,676,869 | B2 * | 3/2010 | Zelnik | A47C 20/00 378/208 |
| 7,697,660 | B2 * | 4/2010 | Ning | A61B 6/032 378/37 |
| 7,763,864 | B2 * | 7/2010 | Formenti | A61B 6/0414 128/845 |
| 8,095,204 | B2 * | 1/2012 | Smith | A61B 5/0091 324/637 |
| 8,246,551 | B2 * | 8/2012 | Miller | A61B 10/0275 600/564 |
| 8,272,089 | B1 * | 9/2012 | Stokes | A61G 13/009 5/620 |
| 8,458,835 | B2 * | 6/2013 | Muratalla | A47G 9/1054 5/630 |
| 8,555,437 | B2 * | 10/2013 | Gorovitz | 5/613 |
| 8,832,879 | B2 * | 9/2014 | Rubio | A47C 20/026 5/632 |
| 8,914,925 | B2 * | 12/2014 | Angott | A61B 5/702 128/845 |
| 2002/0170115 | A1 | 11/2002 | Borders | |
| 2002/0170116 | A1 * | 11/2002 | Borders | A61B 6/0457 5/600 |
| 2004/0081273 | A1 * | 4/2004 | Ning | A61B 6/032 378/37 |
| 2004/0088791 | A1 * | 5/2004 | Corbeil | A61B 5/0091 5/601 |
| 2004/0097811 | A1 | 5/2004 | Smith | |
| 2004/0111801 | A1 * | 6/2004 | Marin | A61B 5/0091 5/621 |
| 2004/0171933 | A1 | 9/2004 | Stoller et al. | |
| 2005/0055774 | A1 | 3/2005 | Marin | |
| 2006/0031993 | A1 * | 2/2006 | Riach | A47C 20/026 5/632 |
| 2006/0094950 | A1 * | 5/2006 | Ning | A61B 6/032 600/407 |
| 2006/0112490 | A1 * | 6/2006 | Chausse | A47C 20/026 5/690 |
| 2006/0123546 | A1 | 6/2006 | Horton et al. | |
| 2007/0033735 | A1 | 2/2007 | Formenti | |
| 2008/0005840 | A1 | 1/2008 | Zelnik | |
| 2008/0005841 | A1 * | 1/2008 | Zelnik | A47C 20/00 5/601 |
| 2009/0064413 | A1 | 3/2009 | Sliski et al. | |
| 2009/0211584 | A1 | 8/2009 | Savich | |
| 2010/0069787 | A1 | 3/2010 | Miller | |
| 2010/0299835 | A1 * | 12/2010 | Andrews | A61G 13/009 5/620 |
| 2011/0010863 | A1 * | 1/2011 | Rubio | A47C 20/026 5/652 |
| 2011/0047705 | A1 * | 3/2011 | Gorovitz | A61G 13/009 5/613 |
| 2011/0083278 | A1 * | 4/2011 | Muratalla | A47G 9/1054 5/655.9 |
| 2013/0198960 | A1 * | 8/2013 | Angott | A61B 5/702 5/622 |
| 2014/0058286 | A1 * | 2/2014 | DeFreitas | A61B 6/0435 600/567 |

OTHER PUBLICATIONS

Office Action dated Aug. 25, 2015, in European Patent Application No. 11842380, the corresponding European patent application to the present application.

Office Action dated May 26, 2015, in Australian Patent Application No. 2011329836, the corresponding Australian patent application to the present application.

* cited by examiner

TABLE FOR PERFORMING MEDICAL PROCEDURES

CROSS-REFERENCE TO RELATED APPLICATIONS

A claim of priority is made to U.S. Provisional Patent Application Ser. No. 61/415,022, filed Nov. 18, 2010, entitled MultiCare RSNA 2009 Maximum Comfort Package Presentation, which is incorporated by reference.

BACKGROUND

Screening exams and biopsies are used to detect cancer and other diseases. For example, a mammogram may be obtained to perform a breast cancer screening exam. If an abnormality is detected during the screening exam then a biopsy may be performed. In the case of a breast biopsy the patient's breast is put in compression so that the area of interest associated with the abnormality can be localized. One or more biopsy or "core" tissue samples are then obtained using a biopsy needle. Maintaining position with the breast in compression for the duration of the biopsy can be uncomfortable for the patient.

SUMMARY

In accordance with one aspect of the invention an apparatus comprises: a table top including a rigid platform with an opening for receiving one of a plurality of interchangeable inserts, each insert including a rigid member and a port through which a portion of a patient's body extends during a medical procedure, wherein a first one of the interchangeable inserts is characterized by a different size port than a second one of the interchangeable inserts; and a base including an upright pillar member connected to the table top, the pillar member being positioned to one side of the table top such that an area beneath the table top is available for positioning equipment for performing the medical procedure.

In accordance with another embodiment of the invention a method comprises: configuring a table for a biopsy procedure by selecting one of a plurality of interchangeable inserts, each insert including a rigid member and a port through which a portion of a patient's body extends during a medical procedure, wherein a first one of the interchangeable inserts is characterized by a different size port than a second one of the interchangeable inserts, and mounting a selected insert in a corresponding opening in the table.

The interchangeable inserts and other features enhance patient comfort and facilitate performance of medical procedures such as breast biopsies. For example, an insert having a port size corresponding to the size of the breast of the patient may be selected to provide better support for the patient. An alternative insert having an asymmetrical opening may be selected to accommodate the patient's arm when it is desirable to position both the arm and breast of the patient below the table top. Furthermore, the area of the insert proximate to the perimeter of the port may include flexible material or padding. The table top may be contoured such that symmetrical distal end sections are elevated relative to a central section to support the patient in multiple positions. A removable and rotatable pad may be placed over the insert. An end portion for padding the hip of the patient is thicker than an end portion for padding the head/neck of the patient.

DETAILED DESCRIPTION

Figure 1:
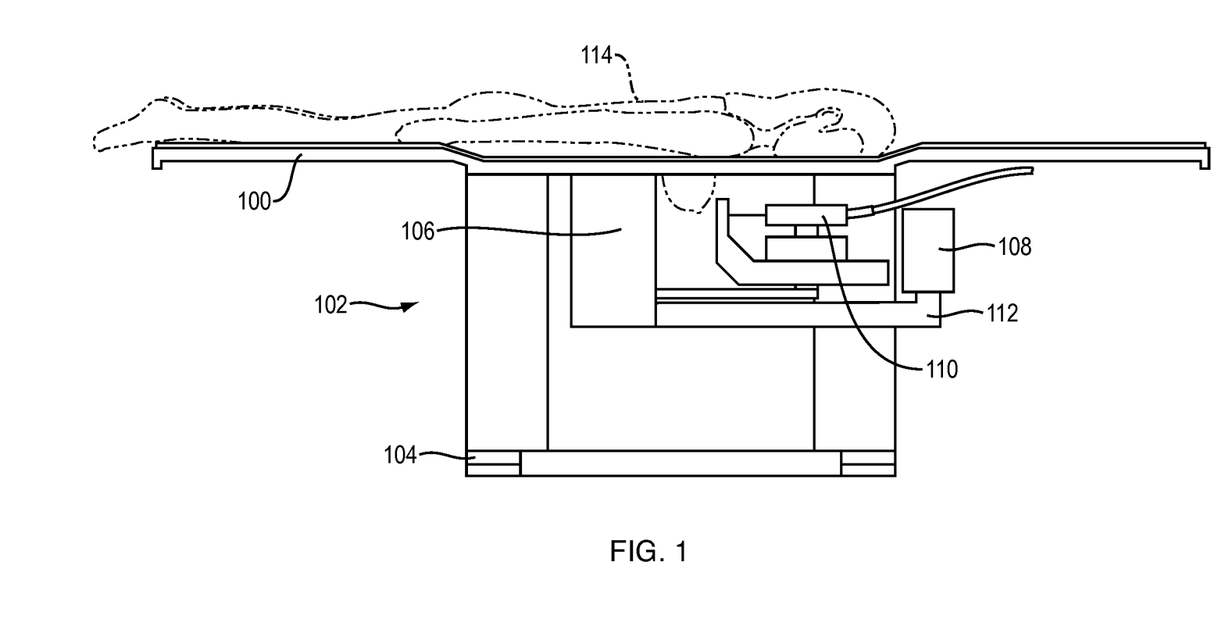
FIGS. 1 and 2 illustrate a table for performing medical procedures such as breast biopsies.
Figure 2:
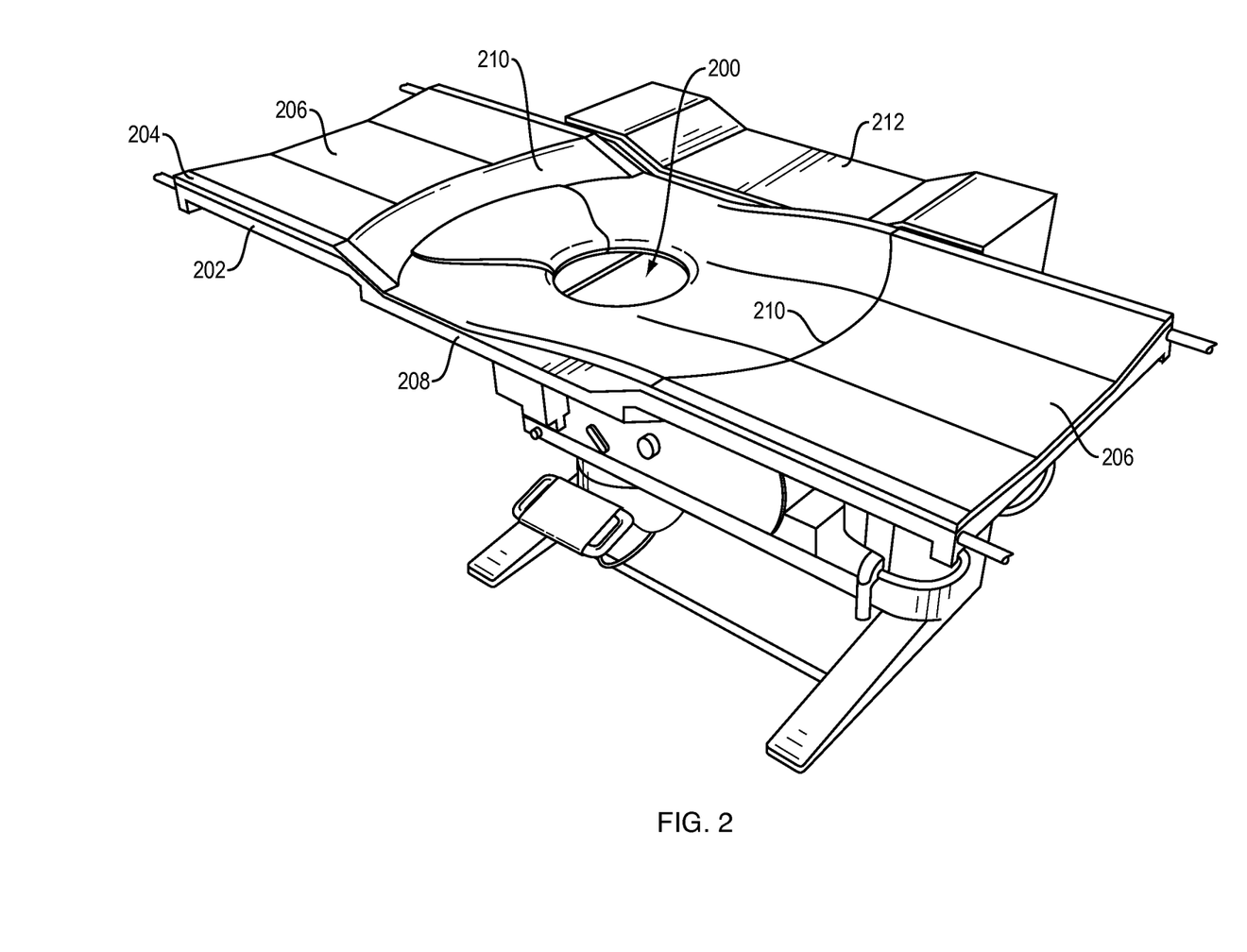
Figure 3A:
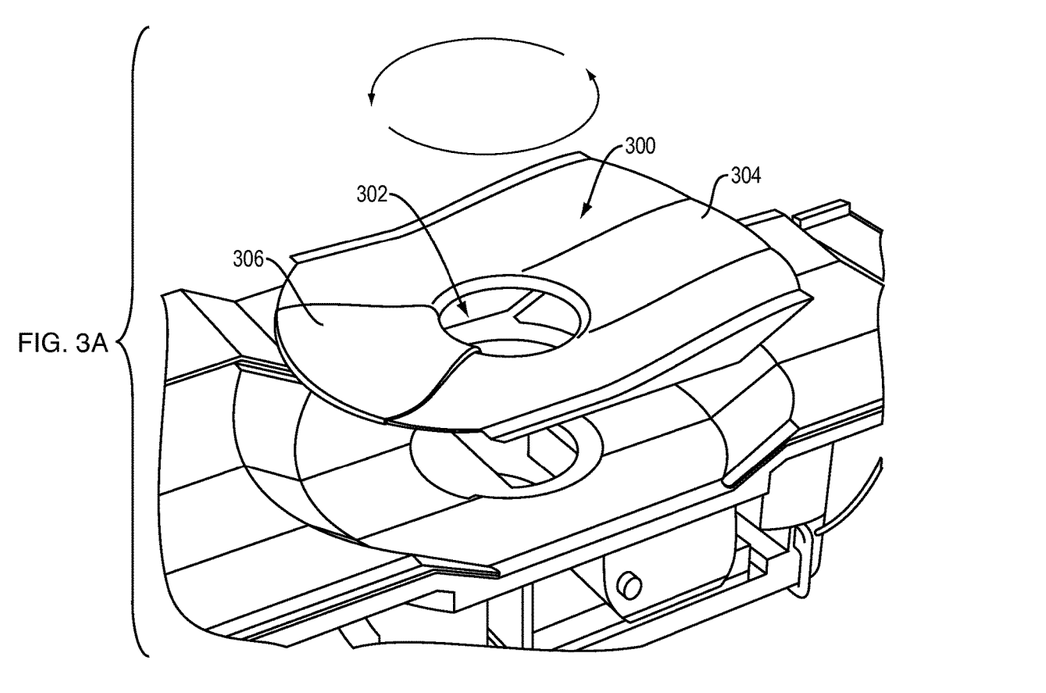
FIGS. 3A and 3B illustrate a removable pad.
Figure 3B:
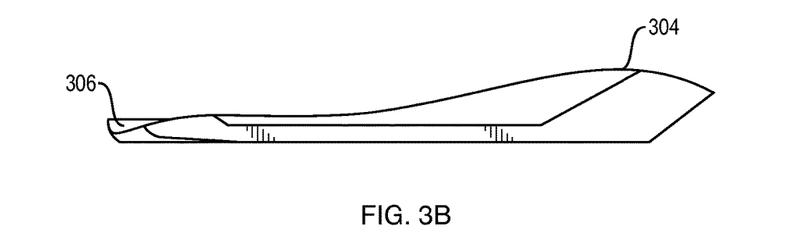

FIGS. 1 and 2 illustrate a table for performing medical procedures such as breast biopsies. The table includes a top 100 which is supported by a base 102. The table top includes a rigid platform 202 at least partially covered with padding 204. An opening 200 in the table top referred to as a "port" or "aperture" is provided to enable a portion of the body of the patient to extend below the table top. The supporting base includes legs 104 and an upright pillar member 106 via which the base is connected to the table top. The pillar is positioned to one side of the table top such that an area beneath the table top is available for positioning both a portion of the body of the patient and equipment for performing the medical procedure. For example, x-ray imaging equipment 108, a biopsy needle 110 and a needle guidance system may be mounted below the table top. The x-ray imaging equipment includes an x-ray source oriented normal to an x-ray detector. The x-ray source is mounted on a c-arm 112 which pivots such that the x-ray source is movable in an arc to enable generation of stereotactic images. Tubing couples the biopsy needle a vacuum console and filter for capturing excised tissue samples.

A patient 114 undergoing a breast biopsy procedure is oriented in a prone position on the table top such that the breast to be biopsied extends through the port. The breast is then placed in compression and the area of interest associated with the abnormality is localized with the x-ray imaging equipment 108 positioned below the table top. Positioning information from the x-ray imaging equipment is used to configure a needle guidance system and one or more biopsy or "core" tissue samples are then obtained using the biopsy needle. The tissue samples are then imaged to detect indicators such as calcifications.

The table top 100 is contoured such that symmetrical distal end sections 206 are elevated relative to a central section 208. Either of the elevated sections can help support the legs of the patient, thereby allowing 180 degree repositioning of the patient. The central section supports the head, abdomen and hip of the patient. Transitions 210 between the end sections and the central section are angled to provide more comfortable head, abdomen and hip support than an abrupt change of elevation. The top 212 of the pillar member is contoured to match the profile of the table top, e.g., the end sections, central section and transitions. The contours may be formed in either or both of the rigid platform and the padding. Contours help avoid the occurrence of pressure points and unsupported points which tend to cause patient discomfort.

Referring to FIGS. 1, 2, 3A and 3B, the entire table top is covered with padding to enhance patient comfort. The padding may include one or more foam layers having different characteristics. For example, the padding may include visco-elastic polyurethane "memory" foam and other types of foam. Memory foam is advantageous because it provides comfort but is also relatively thin when compressed under the weight of the patient, which can be helpful because the patient's breast must extend sufficiently below the table. In one embodiment the table top padding includes multiple foam pads. For example, foam pads covering the distal end sections 206 may be permanently attached to the table top. A removable pad 300 may be placed over the central section of the table top. The removable pad includes an opening 302 which is positioned over the port. An end portion 304 for padding the hip of the patient is thicker than an end portion 306 for padding the head/neck of the patient. The ends of the removable pad are angled to match transitions in the permanently attached pads. The removable pad can be rotated 180 degrees when the patient is repositioned by 180 degrees.

Figure 4:
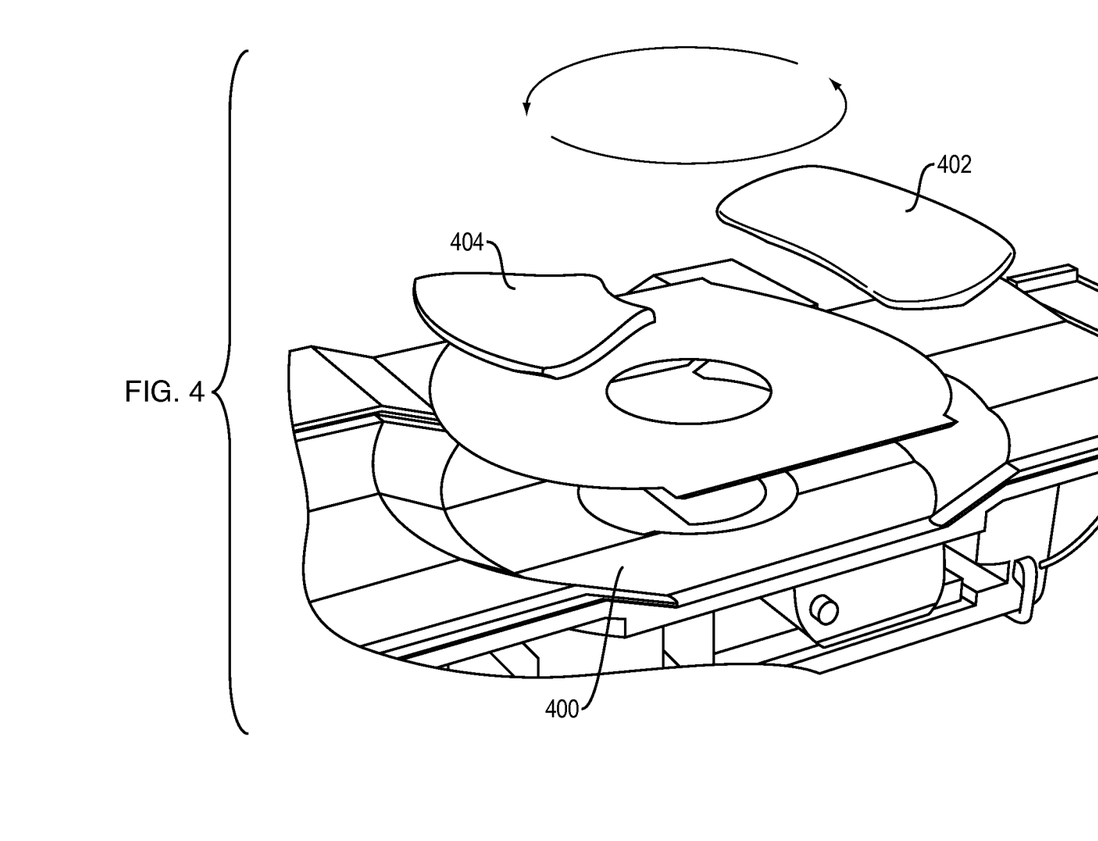
FIG. 4 illustrates an alternative embodiment of the removable pad.

Referring now to FIG. 4, in an alternative embodiment the removable pad includes three separate sections. A ring-shaped base section 400 covers the area of the table top between the port and the transitions of the permanently attached pads. The table may be equipped with a kit including multiple base section pads characterized by different thicknesses. The thickness of the pad can be selected for both comfort and optimal positioning of the patient's breast because thicker padding tends to keep the patient elevated relative to thinner padding. A hip pad 402 and a head/neck pad 404 are positioned on top of the base section. The positions of the hip and head/neck pads are swapped when the patient is repositioned by 180 degrees.

Figure 5:
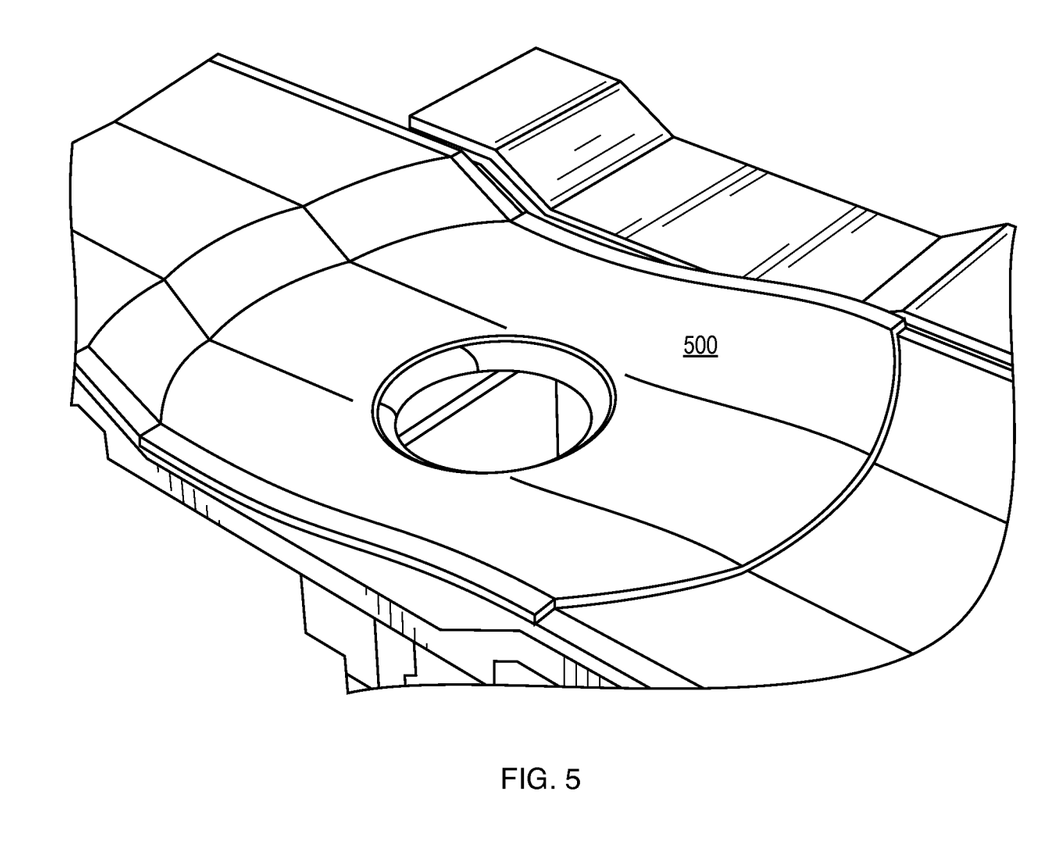
FIG. 5 illustrates an auxiliary pad.
Figure 6:
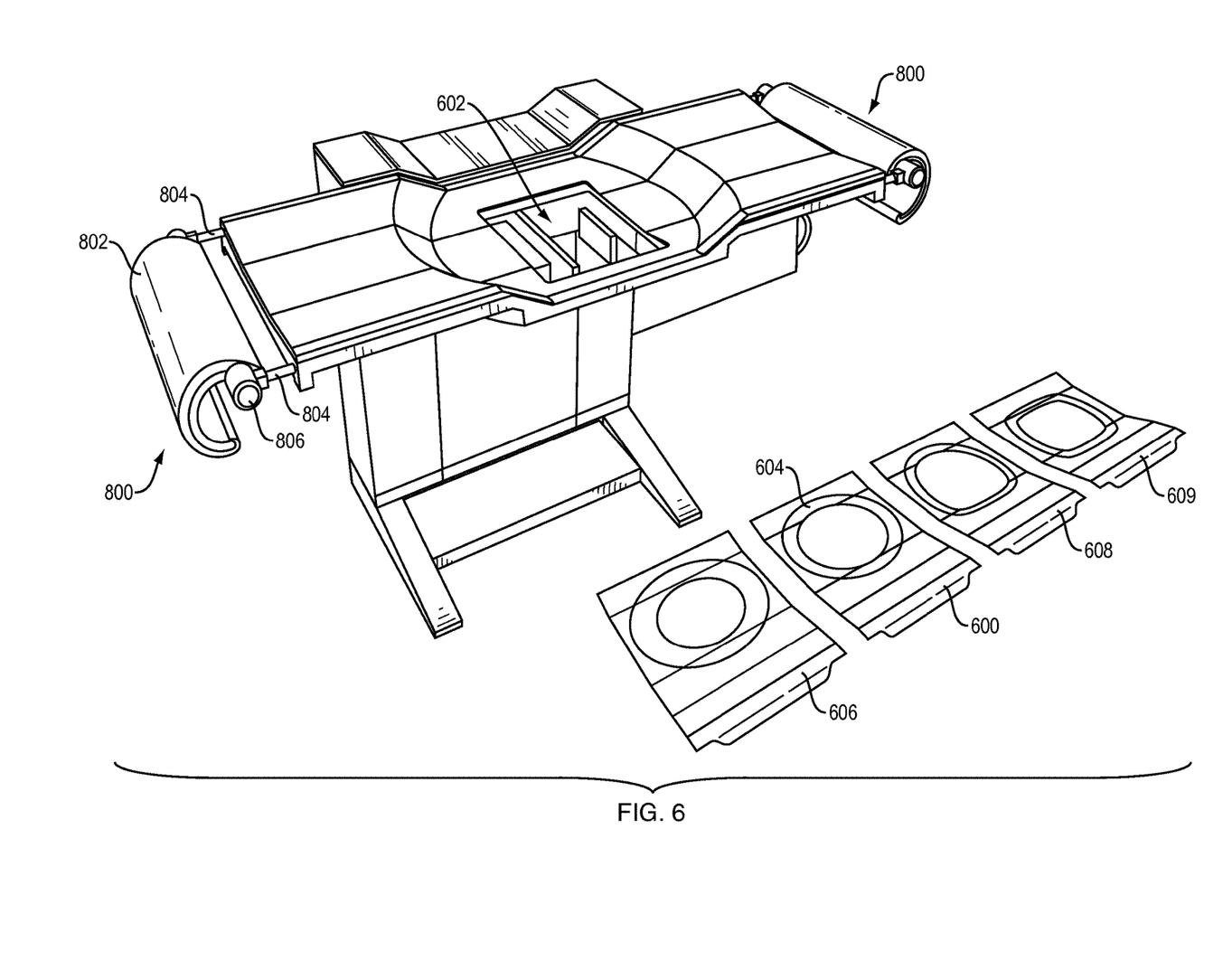
FIG. 6 illustrates a removable insert.

As shown in FIG. 5, an additional layer of padding 500 may be provided to elevate the patient or further enhance comfort. The additional layer of padding is disposed over the removable pad. An opening in the center substantially matches the opening in the removable pad As shown in FIG. 6, the port may be formed in a removable insert 600. The insert includes a rigid sheet member which is formed to fit into a corresponding opening 602 in the table top. A flange or other feature in the table top supports the insert. The insert should be constructed of a material capable of supporting the patient without excessive flex. An area of the insert proximate to the perimeter of the opening includes integral padding 604 and may include a ring of material which is characterized by greater flex than other portions of the insert. An advantage of using removable port inserts is that the size and shape of the insert can be selected to better accommodate the patient. For example, an alternate insert 606 having a larger or smaller diameter opening may be selected based on the size of the patient's breast. Furthermore, an alternative insert 608 having an asymmetrical opening may be selected to accommodate the patient's arm when it is desirable to position both the arm and breast of the patient below the table top. Another alternative is a rectangular insert with rounded corners 609.

Figure 7:
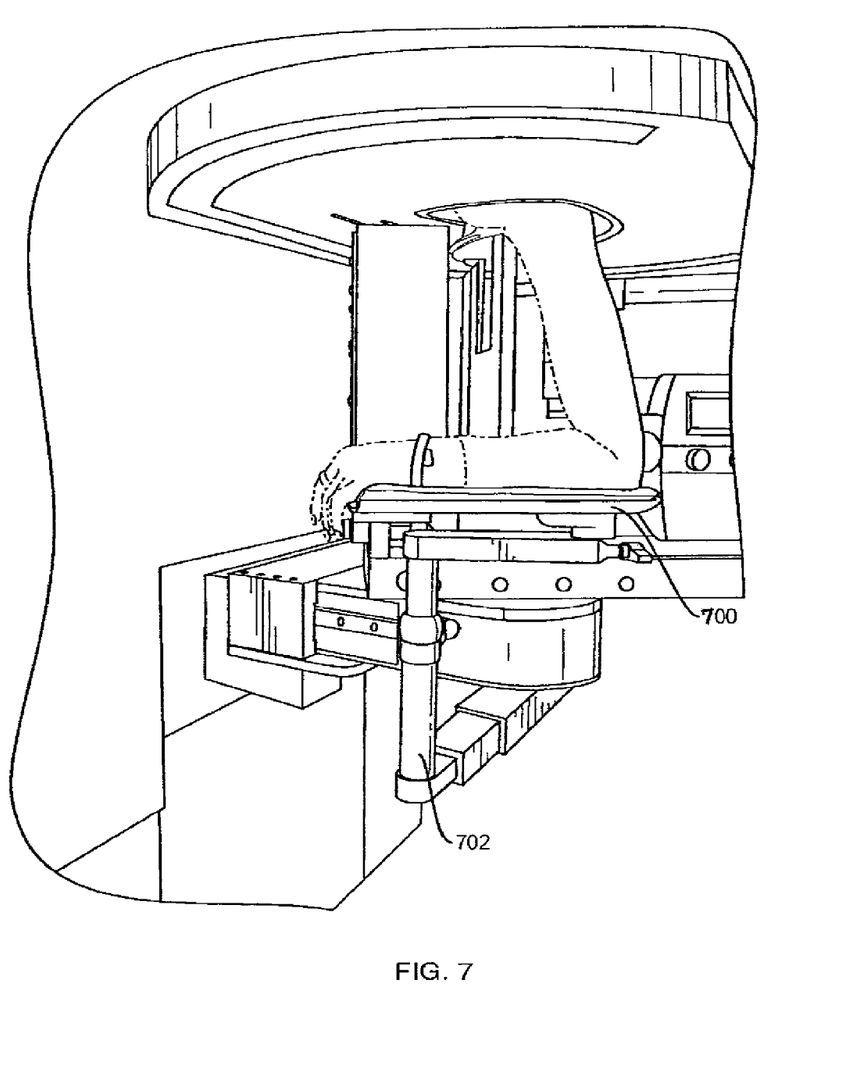
FIG. 7 illustrates an arm support feature.

Referring now to FIG. 7, the table may include a feature for supporting the patient's arm below the table top. The arm support feature includes a horizontal platform 700 which is connected to a shaft member 702. The shaft member is connected to the pillar via an extension arm having a clamp. The shaft member can be moved both rotationally and vertically when the clamp is loosened, thereby allowing three-dimensional adjustment of the position of the horizontal platform.

Figure 8:
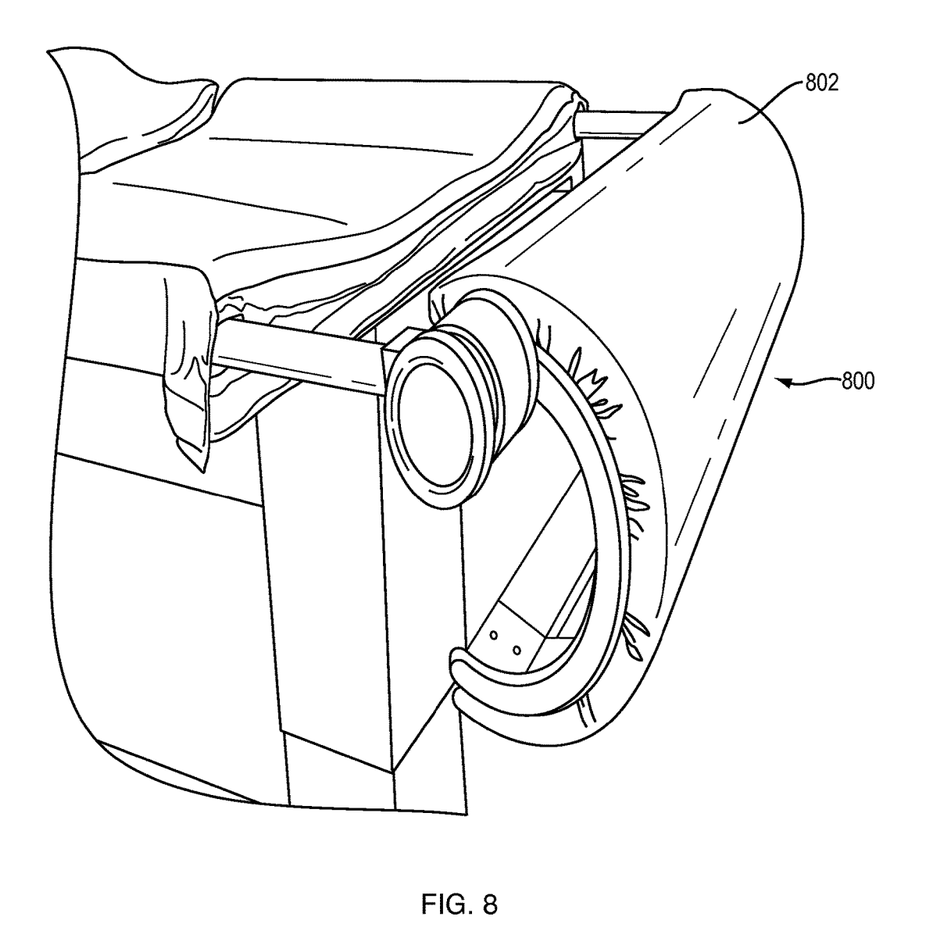
FIG. 8 illustrates an adjustable foot/leg support.

Referring now to FIGS. 6 and 8, extendable foot/leg supports 800 may be provided at both ends of the table top. Each support includes a rounded or arcuate padded member 802 connected to the table via two support shafts 804. The support shafts enable horizontal repositioning. In particular, the support shafts can be moved slidably and secured in position when the foot/leg support is a desired distance from the table top. Typically, patients prefer to have support somewhere between the top of the foot and shin. The foot/leg support also includes a vertical position feature. The support shafts are connected to one end of the padded member via a rotatable joint 806. Consequently, the elevation of the padded member can be adjusted by rotating the padded member at an axis defined by the rotatable joints. The joint includes a locking feature for securing the padded member in position when a suitable elevation is attained. In one embodiment the locking feature includes a knob with detents which engage projections under spring pressure to enable the padded member to be secured in one of a finite set of positions.

While the invention is described through the above exemplary embodiments, it will be understood by those of ordinary skill in the art that modification to and variation of the illustrated embodiments may be made without departing from the inventive concepts herein disclosed. Moreover, while the preferred embodiments are described in connection with various illustrative structures, one skilled in the art will recognize that the system may be embodied using a variety of specific structures. Accordingly, the invention should not be viewed as limited except by the scope and spirit of the appended claims.

The invention claimed is:

1. Apparatus comprising:
   a table top including a rigid platform with an opening;
   a plurality of interchangeable inserts, each of said plurality of interchangeable inserts being alternatively positionable in the opening of the table top, each insert including a rigid member and a port through which a portion of a patient's body extends during a medical procedure, wherein a first one of the interchangeable inserts is characterized by a different size port than a second one of the interchangeable inserts;
   a removable pad removably mounted over the interchangeable insert in the opening, the removable pad, when removably mounted over the interchangeable insert in the opening, permitting the portion of the patient's body to extend through the port of the interchangeable insert; and
   a base including an upright pillar member connected to the table top, the pillar member being positioned to one side of the table top such that the table top is cantilevered and an area beneath the table top is accessible for positioning equipment for performing the medical procedure.

2. The apparatus of claim 1 wherein the second one of the interchangeable inserts is characterized by an asymmetrical opening.

3. The apparatus of claim 1 wherein the table top is contoured such that symmetrical distal end sections are elevated relative to a central section.

4. The apparatus of claim 3 wherein the pillar member is contoured to match elevations of the distal end sections relative to the central section of the table top.

5. The apparatus of claim 1 further comprising first and second foam pads covering first and second distal end sections of the table top.

6. The apparatus of claim 5 wherein the removable pad covers a central section of the table top abutting the first and second distal end sections.

7. The apparatus of claim 6 wherein the removable pad includes a first end portion characterized by greater thickness than a second end portion.

8. The apparatus of claim 1 wherein the removable pad includes a ring-shaped base section, a hip section, and a head/neck section, the ring-shaped base section, the hip section, and the head/neck section being three separate pieces.

9. The apparatus of claim 8 wherein the table top is equipped with multiple base section pads characterized by different thicknesses.

10. The apparatus of claim 1 further including a horizontal platform for supporting a patient's arm below the table top, the platform being three dimensionally repositionable.

11. The apparatus of claim 1 further including first and second extendable supports disposed at first and second distal ends of the table top.

12. The apparatus of claim 11 wherein each support includes a rounded padded member which is rotatable around a non-central axis and securable in multiple rotational positions in order to provide height adjustment.

13. A method comprising:

configuring a table for a biopsy procedure by selecting one of a plurality of interchangeable inserts, each insert including a rigid member and a port through which a portion of a patient's body extends during a medical procedure, wherein a first one of the interchangeable inserts is characterized by a different port size than a second one of the interchangeable inserts, mounting a selected insert in a corresponding opening in the table, and then positioning a removable pad over the selected insert, the removable pad, when positioned over the selected insert, permitting the portion of the patient's body to extend through the port of the selected insert.

14. The method of claim 13 including selecting the interchangeable insert based on patient breast size.

15. The method of claim 13 including selecting an insert characterized by an asymmetrical opening to accommodate a patient's arm.

16. The method of claim 13 wherein the removable pad includes an opening alignable with the port.

17. The method of claim 16 wherein the removable pad is rotatable relative to the selected insert for reversing orientation of the patient's body and is oriented such that a patient's hip will rest on a first end portion characterized by greater thickness than a second end portion.

18. The method of claim 13 wherein the removable pad comprises a ring-shaped base section, a hip section, and a head/neck section, the ring-shaped base section, the hip section, and the head/neck section being three separate pieces.

19. The method of claim 18 including selecting one of a plurality of base section pads characterized by different thicknesses.

20. The method of claim 13 including adjusting a horizontal platform for supporting a patient's arm below the table.

21. The method of claim 13 including extending a first or second support disposed at first and second distal ends of the table.

22. The method of claim 21 including adjusting height of the first or second support by rotating a rounded padded member around a non-central axis.

* * * * *